United States Patent [19]

Kanno et al.

[11] Patent Number: 4,727,417
[45] Date of Patent: Feb. 23, 1988

[54] ENDOSCOPE VIDEO APPARATUS

[75] Inventors: Masahide Kanno; Masahiko Sasaki; Tetsuo Nonami; Shinichi Kato; Yutaka Konomura; Yoshikazu Ichikawa, all of Tokyo, Japan

[73] Assignee: Olympus Optical Co., Ltd., Tokyo, Japan

[21] Appl. No.: 48,671

[22] Filed: May 11, 1987

[30] Foreign Application Priority Data

May 14, 1986 [JP] Japan .................. 61-109760
May 14, 1986 [JP] Japan .................. 61-109761
Jun. 27, 1986 [JP] Japan .................. 61-150854

[51] Int. Cl.$^4$ .................. A61B 1/04; H04N 7/18
[52] U.S. Cl. .................. 358/98; 128/4; 358/102; 358/181; 358/183; 358/909; 360/14.2
[58] Field of Search .............. 358/98, 181, 183, 102, 358/903, 909; 128/4, 6; 360/14.1, 14.2, 14.3, 5, 35.1

[56] References Cited

U.S. PATENT DOCUMENTS 4,491,874 1/1985 Yamamoto .................. 360/14.2
4,654,701 3/1987 Yabe .................. 358/98

FOREIGN PATENT DOCUMENTS 60-206276 10/1985 Japan .
60-206277 10/1985 Japan .

Primary Examiner—Howard W. Britton
Attorney, Agent, or Firm—Frishauf, Holtz, Goodman & Woodward

[57] ABSTRACT

An endoscope video apparatus has an endoscope including a solid-state image sensor, for outputting an endoscopic image signal, a video processor for processing the image signal supplied from the solid-state image sensor and outputting a video signal, an image file unit for recording the video signal, and an input section for inputting retrieval data corresponding to the video signal recorded in the image file unit. A control section discriminates the presence/absence of retrieval data input from the input section. A control circuit operates an alarm unit by discrimination data representing the absence of retrieval data.

17 Claims, 9 Drawing Figures

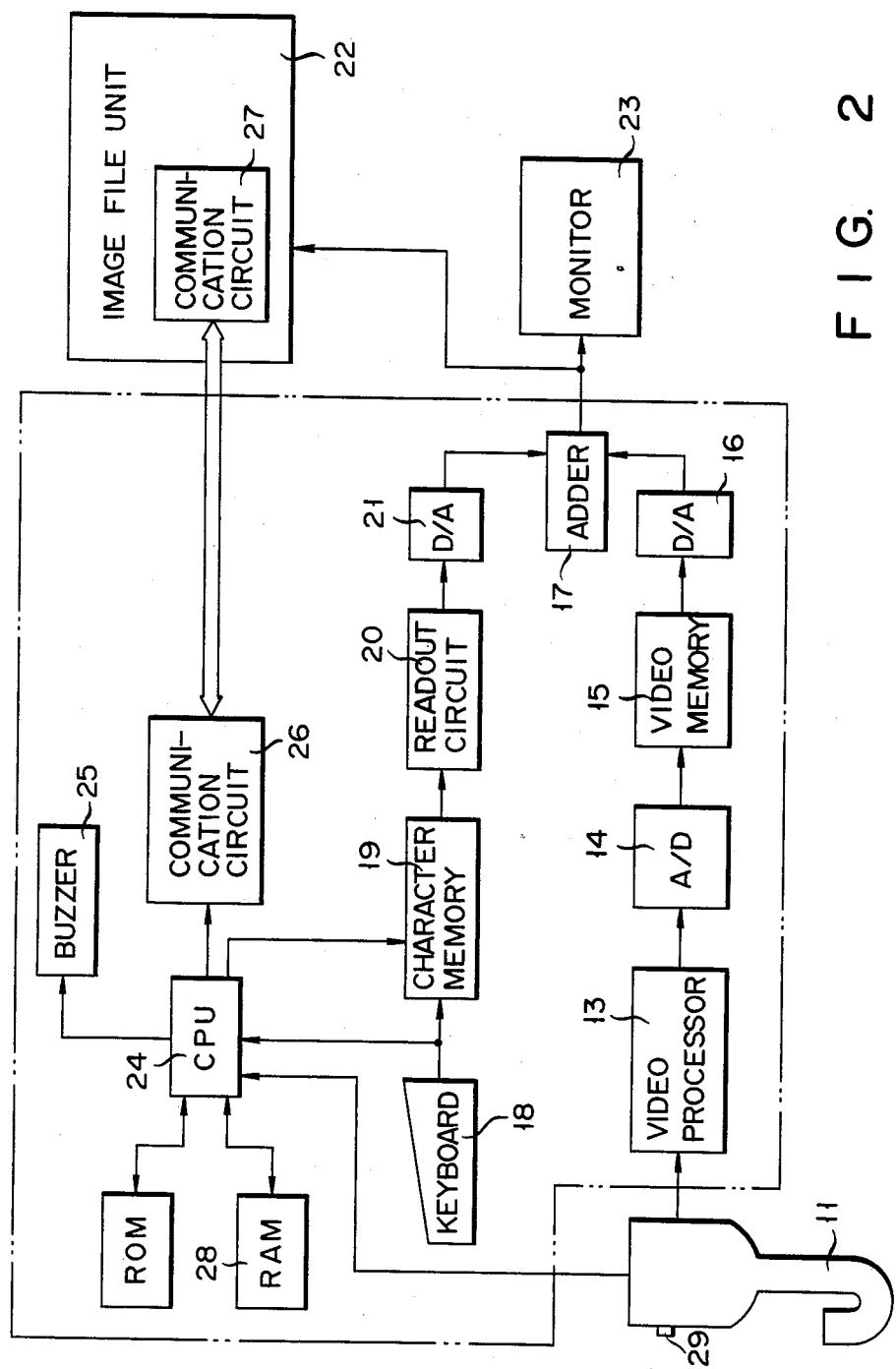
F I G. 2

FIG. 3
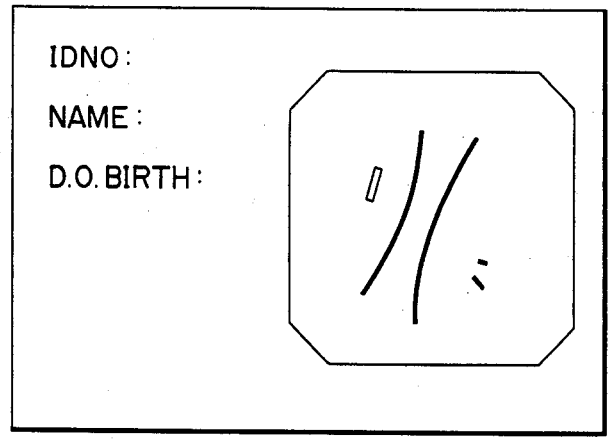
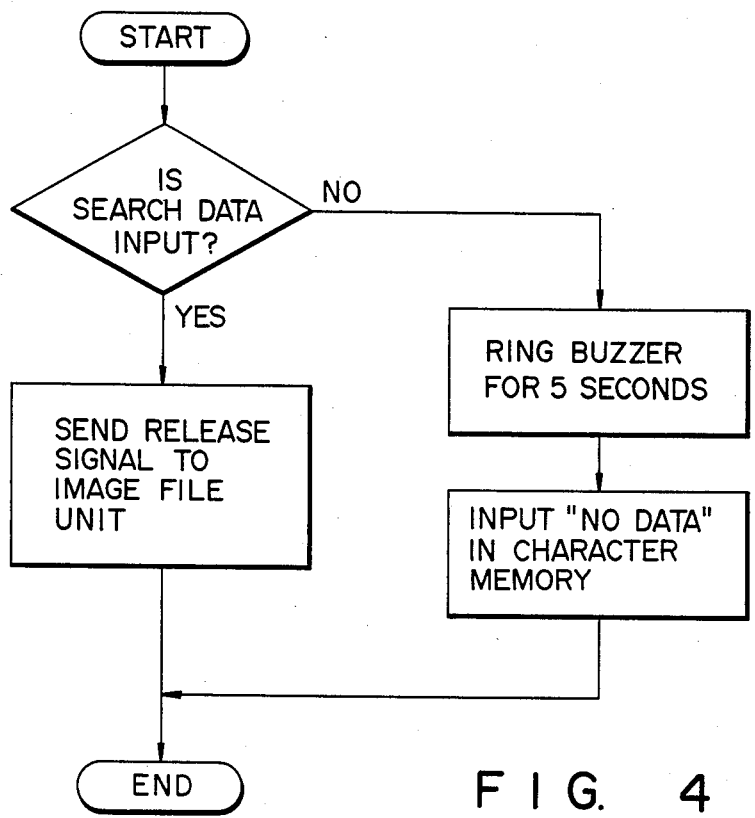
FIG. 4

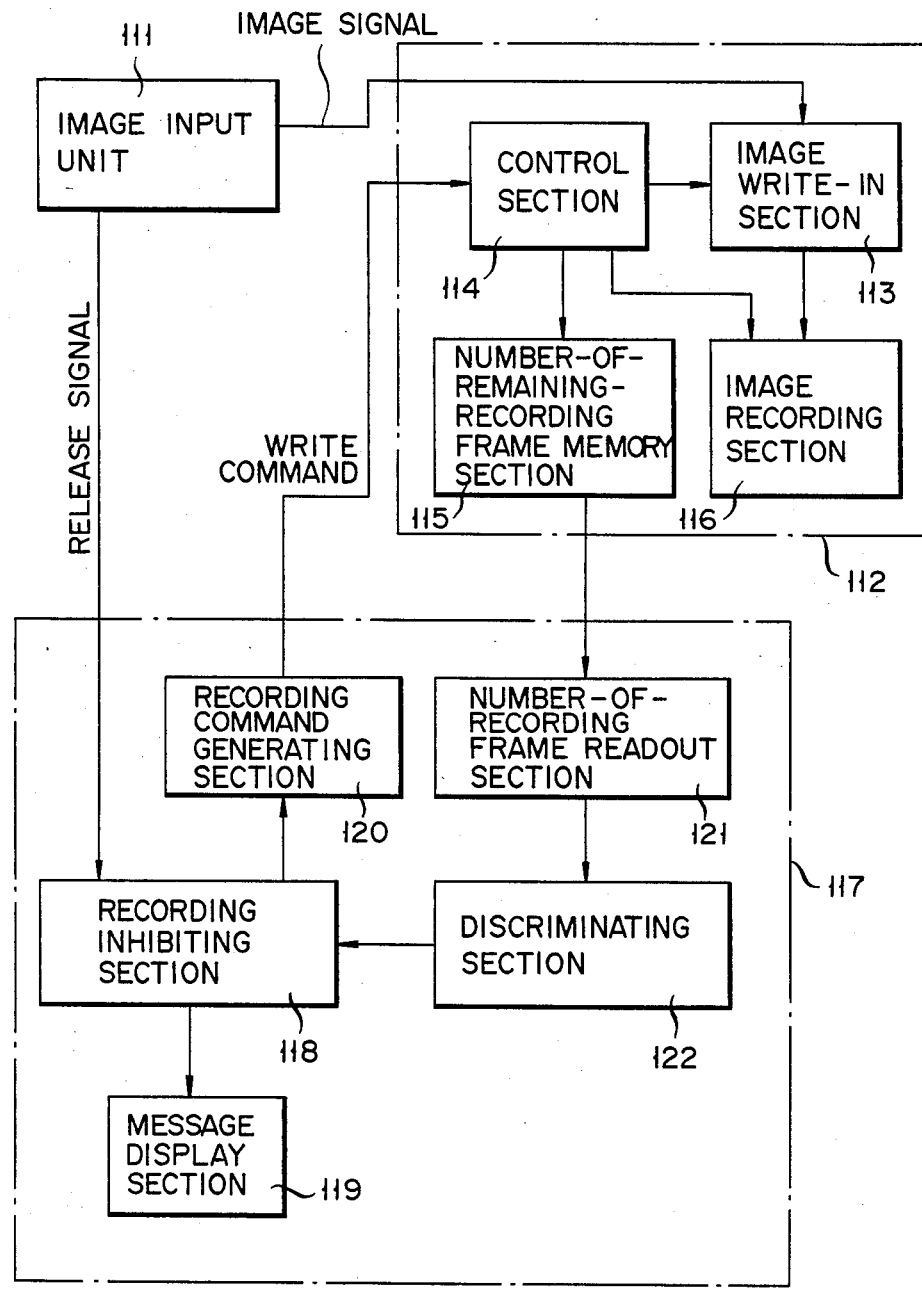
F I G. 5

FIG. 7

| EXAMINING | IMAGE RECORDING | SEARCHING | COMMUNICATING |
|---|---|---|---|
| NEXT FRAME | PRECEDING FRAME | NEXT EXAMINATION | PRECEDING EXAMINATION |

\*\*\* COMMUNICATION PROGRAM \*\*\*

ID NO.
NAME
DATE OF BIRTH
DATE OF EXAMINATION

IMAGE NO. /

100%

0%

MENU

ENDOSCOPE VIDEO APPARATUS

BACKGROUND OF THE INVENTION

The present invention relates to an endoscope video apparatus using an electronic endoscope.

When an endoscopic image of a body cavity, picked up by an electronic endoscope incorporating a solid-state image pickup element, is to be recorded in an image file unit, retrieval data required for retrieving the endoscopic image later is input from the image file unit. Since the image file unit is separated from the electronic endoscope, in order to input the retrieval data, the user must move between the image file unit and the electronic endoscope. In order to eliminate this inconvenience, an endoscope video apparatus has been developed which has a communication function between the image file unit and an endoscope light source unit to which an endoscope is connected. Retrieval data is input from the endoscope light source unit and transmitted to the image file unit via a communication line.

The endoscope video apparatus having the communication function eliminates a need for the user to move between the image file unit and the electronic endoscope. However, the user may sometimes forget to input retrieval data from the endoscope, and in this case it is impossible to retrieve an endoscopic image later because no retrieval data has been recorded.

SUMMARY OF THE INVENTION

It is an object of the present invention to provide an endoscope video apparatus having a function to prevent recording of an image to an image file unit unless retrieval data has been input.

According to this invention, a retrieval data input discriminator for discriminating presence/absence of retrieval data supplied from an input section for inputting retrieval data, a communication circuit for communicating with an image file unit as an endoscopic image record retrieval unit, and an alarming member for alarming that no retrieval data is input are provided to a video processor connected to an electronic endoscope. When retrieval data is not input, an alarm by the alarming member or an alarm display on a display is performed.

BRIEF EXPLANATION OF THE DRAWINGS

FIG. 2 is a detailed block diagram of the endoscope video apparatus;

FIG. 3 is a view of a monitor screen;

FIG. 4 is a flow chart for explaining the operation for discriminating presence/absence of retrieval data;

FIG. 5 is a block diagram of an endoscopic image file unit;

FIG. 7 is a view of a display section shown in FIG. 5;

DETAILED DESCRIPTION OF THE PREFERRED EMBODIMENT

Figure 1:
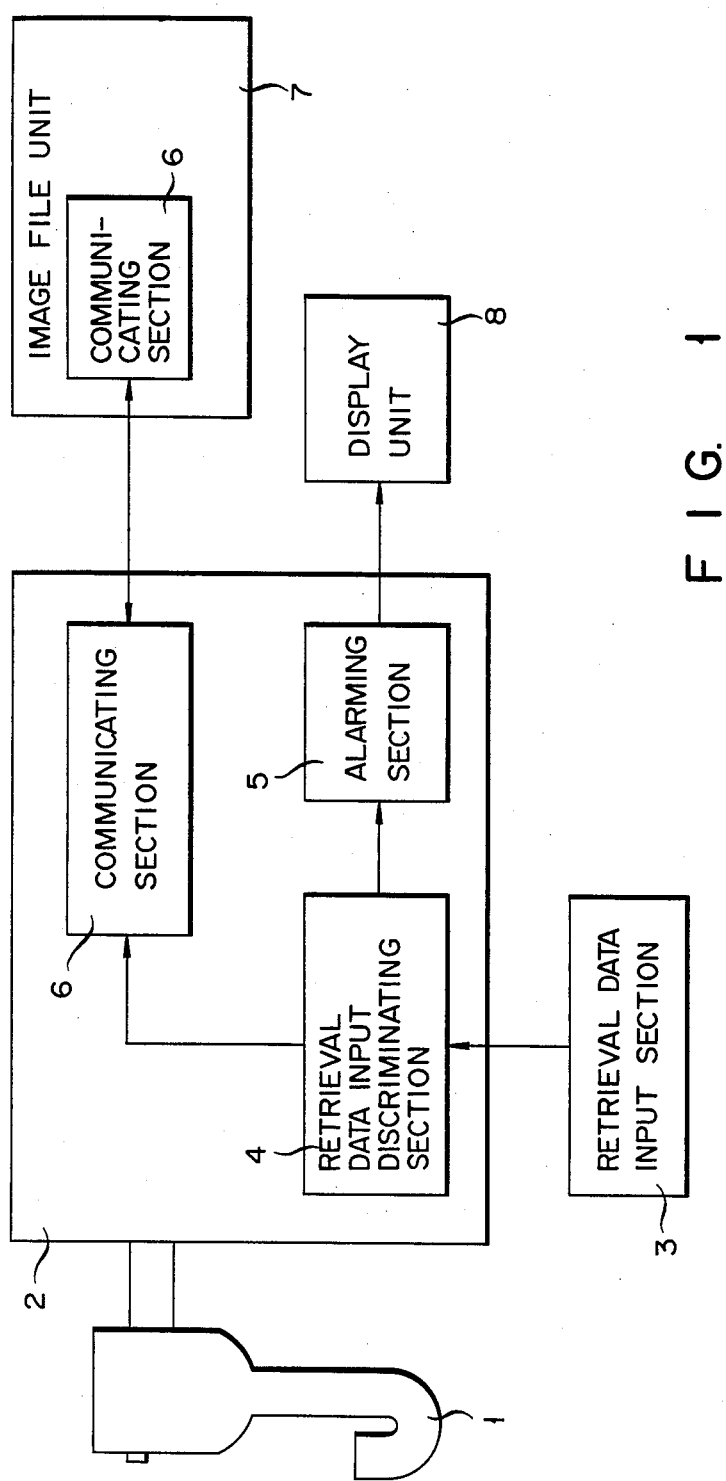
FIG. 1 is a circuit diagram of a main part of an endoscope video apparatus according to the present invention.

An endoscope video apparatus having video endoscope light source 2 which is connected to electronic endoscope 1 includes retrieval data input discriminating circuit 4, communicating circuit 6, and alarming unit 5, as shown in FIG. 1. Retrieval data input discriminating circuit 4 discriminates presence/absence of retrieval data supplied from an input circuit for inputting retrieval data. Communicating circuit 6 communicates with an image file unit as an endoscopic image recording/retrieval unit. Alarming unit 5 alarms that no retrieval data is input. When retrieval data is not input, alarming unit 5 generates an alarm or alarm display is made on display unit 8. Therefore, image data without retrieval data cannot be recorded, and a retrieval disabled state does not occur when retrieval is later performed.

According to an endoscope video apparatus shown in FIG. 2, the image output terminal of electronic endoscope or video endoscope 11 is coupled to video processor 13 in video endoscope light source unit 12. The output terminal of processor 13 is connected to video memory 15 through A/D converter 14. The output terminal of video memory 15 is connected to adder 17 through D/A converter 16.

Keyboard 18 for inputting retrieval data is connected to character memory 19. Data in character memory 19 is read out by readout circuit 20. The output terminal of readout circuit 20 is connected to adder 17 through D/A converter 21. Adder 17 is coupled to image file unit 22 and monitor 23.

The output terminal of keyboard 18 is connected to CPU 24 together with the release signal output terminal of video endoscope 11. The output terminals of CPU 24 are connected to buzzer 25, communication circuit 26, and character memory 19. Communication circuit 26 is connected to communication circuit 27 in image file unit 22. CPU 24 is also connected to a ROM and RAM 28. In the endoscope video apparatus with the above arrangement, when a power switch of video endoscope light source 12 is turned on, CPU 24 starts operation, and the item names (ID.NO, NAME, and D.0.BIRTH) of retrieval data are input in character memory 19 in accordance with a predetermined format. The item names are read out by readout circuit 20, converted into analog signals by D/A converter 21, and input to adder 17.

An image signal from electronic endoscope 11 is signal-processed by video processor 13 and stored in video memory 15 through A/D converter 14. The video data of video memory 15 is converted into analog video signals by D/A converter 16 and input to adder 17. Adder 17 adds the endoscope video signal and item name signals, and inputs the obtained sum signal to monitor 23 to cause monitor 23 to display item names, as shown in FIG. 3, and stores them in image file unit 22.

The user inputs retrieval data through keyboard 18 as he monitors the image shown in FIG. 3. In data inputting, when the date of birth (BIRTH) is to be input, a year in Showa (S) period, a year in Taisho (T) period, and a year in Meiji (M) period are indicated as 1 or more, 1 to 15, and 1 to 45, respectively, a month is indicated by 1 to 12, and the day of the month is indicated by 1 to 31.

Input retrieval data is input to character memory 19 and stored therein. Retrieval data read out from character memory 19 is converted as a composite endoscopic image and displayed on monitor 23. The retrieval data input from keyboard 18 is stored in RAM 28 as it is input to CPU 24, and at the same time transmitted to image file unit 22 through communication circuit 26.

When the user finds a required endoscopic image while monitoring the screen of monitor 23, he operates release switch 29 provided to video endoscope 11. A release signal generated at this time is sent to CPU 24. Upon reception of the release signal, CPU 24 executes an operation to discriminate presence/absence of retrieval data in accordance with the flow chart shown in FIG. 4. More specifically, whether retrieval data is input or not is discriminated by determining whether retrieval data is stored in RAM 28 prior to the release operation. If YES, CPU 24 sends the release signal to image file unit 22 through communication circuits 26 and 27. In response to the release signal, image file unit 22 records the required endoscopic image together with the retrieval data on a recording medium.

If NO in the input discrimination of the retrieval data, i.e., if retrieval data is not stored in RAM 28, CPU 24 sounds buzzer 25 for 5 seconds and inputs characters "NO DATA" to character memory 19. The characters "NO DATA" are read out by readout circuit 20 and supplied to monitor 23 through D/A converter 11 and adder 17. Monitor 23 displays the characters "NO DATA". This display and sounding of buzzer 25 alerts the user that retrieval data is not input. Upon reception of the alarm, the user can input retrieval data through keyboard 18.

Whether retrieval data is input or not is discriminated in this manner. When retrieval data is not input, an alarm is generated to prevent filing of the endoscopic image, so that an image which cannot be retrieved at the time of retrieval may not be recorded.

Image file unit 22 can be incorporated into light source unit 12. In this case, communication circuits 26 and 27 can be dispensed with, and the retrieval data is supplied directly from CPU 24 to image file unit 22.

When an endoscopic image is recorded on an optical disk, images of 20 to 25 frames are usually picked up for a single endoscope diagnosis and are recorded on the optical disk. In image recording, when the number of remaining recordable frames of the optical disk is smaller than 20 to 25 at the start of endoscope diagnosis, the recording capacity of the optical disk may overflow during diagnosis, i.e., during photographing, and examination must be stopped. This may cause pain to the patient. In order to eliminate such an inconvenience, countermeasures are taken as follows. More specifically, referring to FIG. 5, the image signal output terminal of image input unit 111 is connected to image write-in section 113 in image recording unit 112. Write-in section 113 records an image signal in image recording section 116 under the control of control section 114. Recording section 116 has, e.g., an optical disk. Control section 114 is connected to number-of-remaining frame memory section 115 for storing the number of recordable frames, i.e., the number of remaining recording frames, of the optical disk, and reads out data representing the number of remaining recording frames from recording section 116 and inputs it to memory section 115.

The output terminal of number-of-remaining-recording frame memory section 115 is connected to number-of-remaining-recording frame readout circuit 121 in control circuit section 117. The output terminal of readout circuit 121 is connected to discriminator 122. Discriminator 122 discriminates whether the number of remaining recording frames is equal to or less than a predetermined value, e.g., 30. The discriminator output terminal of discriminator 122 is connected to recording inhibiting circuit 118. Inhibiting circuit 118 outputs a message representing insufficient number of recording frames and a recording command signal to message display section 119 and recording command generator 120 in accordance with the discrimination result of discriminator 122. Inhibiting circuit 118 supplies a trigger signal to generator 120 in response to the release signal from image input unit Generator 120 outputs a write command signal to control section 114.

Figure 6:
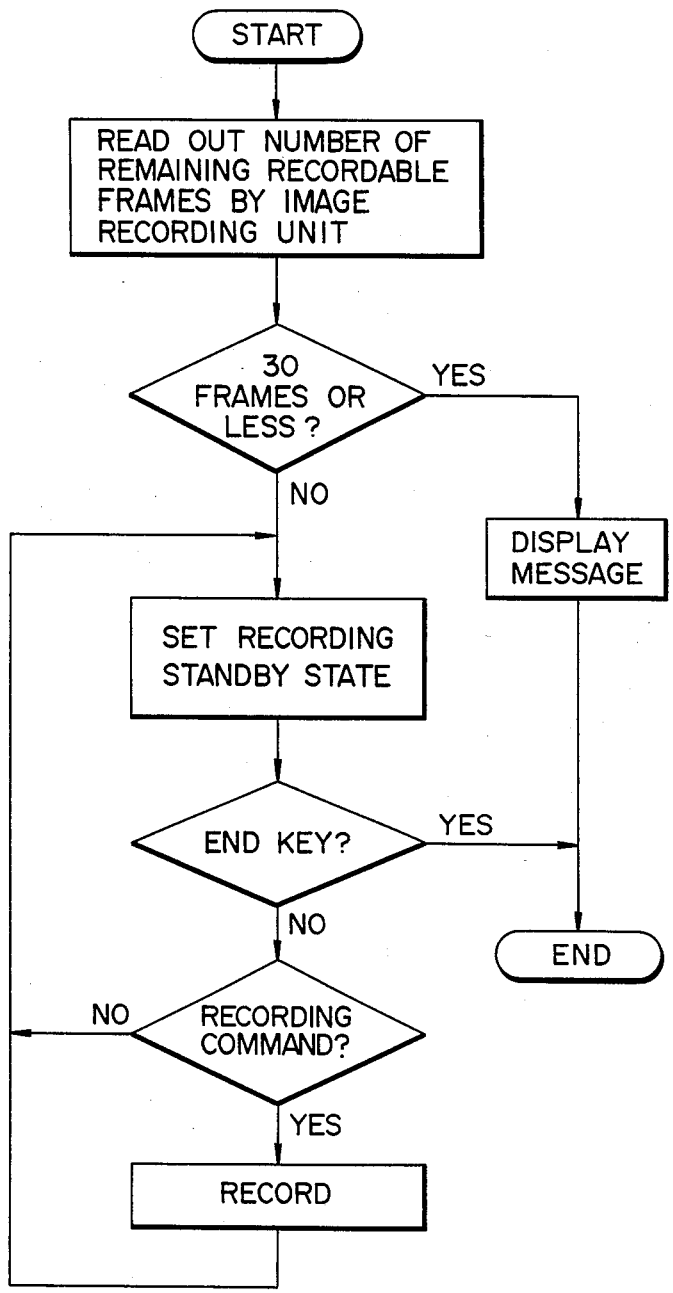
FIG. 6 is a flow chart for explaining the operation of the unit shown in FIG. 5.

When the above apparatus is started as shown in the flow chart of FIG. 6, control section 114 detects the remaining capacity of image recording section 116 first, and inputs the number of remaining memory frames in memory section 115 so that recording section 115 records the number of remaining frames.

The number-of-remaining frame data of number-of-remaining-recording frame memory section 115 is read out by number-of-recording frame readout circuit 121 and output to discriminator 122. Discriminator 122 compares the readout number of remaining frames with a predetermined number, e.g., 30. When the number of remaining frames is not 30 or less, discriminator 122 outputs a recording delay signal to recording inhibiting circuit 118. In this case, when a release signal is supplied to inhibiting circuit 118, recording command generator 120 outputs a write command signal to control section 114 in image recording unit 112.

Control section 114 outputs a write-in command signal to image write-in section 113. Write-in section 113 records an image signal from image input unit (electronic endoscope) 111 in image recording section 116. When 1-frame recording is completed, the next 1-frame image signals are recorded on the optical disk in recording section 116 in response to a release signal. In this case, 1-frame image signals are recorded on one track of the optical disk. When 20- to 50-frame image data are recorded in this manner and an end key is depressed, a recording operation is ended.

When discriminator 122 discriminates that the number of remaining recording frames is 30 or less, recording inhibiting section 118 outputs a message to message display section 119 to inform that the number of remaining recording frames is insufficient. Display section 119 displays the remaining capacity in its remaining capacity display area as shown in FIG. 7. The remaining capacity can be displayed by using a bar representation or by using different colors. For example, when the remaining capacity is 5,000 to 1,001, 1,000 to 101, and 100 or less, a representation in white characters, yellow characters, and yellow flashing characters, respectively, can be performed.

Upon reception of a discrimination signal representing 30 frames or less, recording inhibiting section 118 inhibits recording command generator 120 to generate a write command signal in order to inhibit image recording. As a result, control section 114 does not supply a write-in command to image write-in section 113, and image data recording by image recording section 116 is inhibited.

Before a start of endoscope diagnosis, the remaining capacity of a recording medium, such as an optical disk, is detected. When the detected remaining capacity is less than a predetermined value, an insufficient remaining capacity is informed, and recording is inhibited. Therefore, a stop of photographing or diagnosis can be prevented during diagnosis because of an insufficient remaining capacity.

Figure 8:
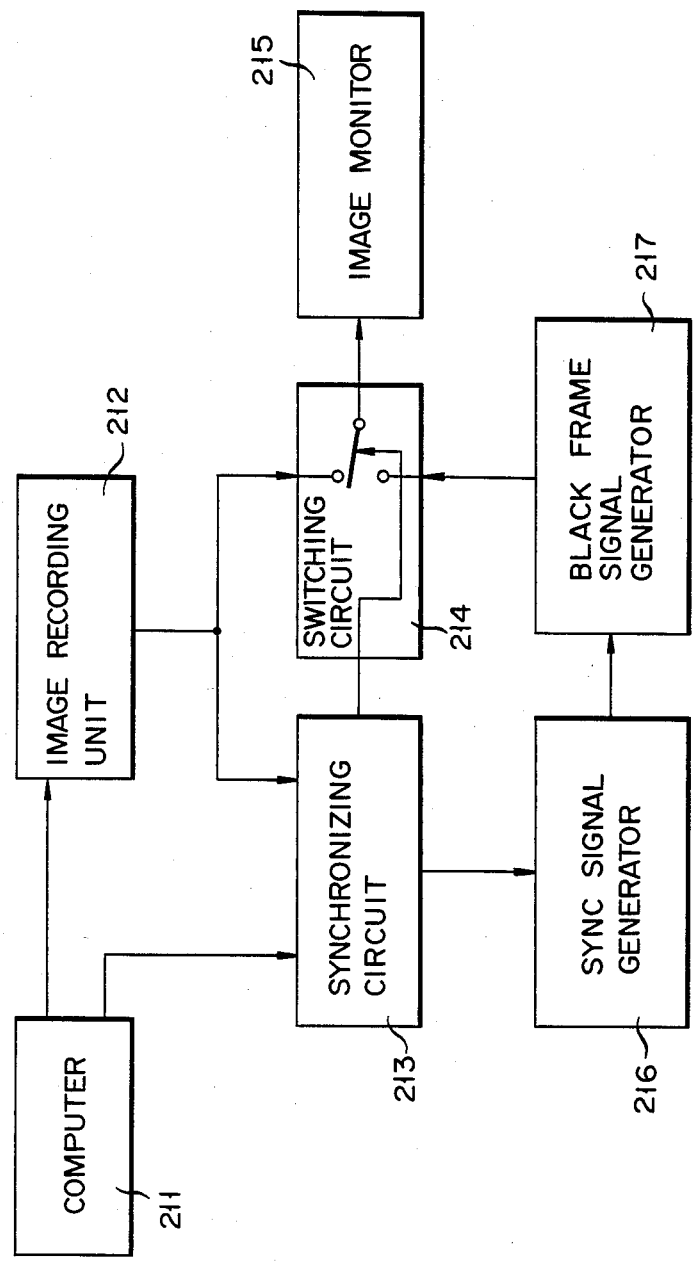
FIG. 8 is a block diagram of the endoscopic image file unit.

Since an image recording/reproducing section and a monitor are directly connected to each other in an imaging apparatus, a non-required image reproduced from an image memory is undesirably displayed before a required image is designated, i.e., before image retrieval. When image retrieval is started and binary signals are displayed on the monitor, since retrieval code data (binary signals) reproduced from a retrieval code track is input in the monitor as video signals, a black-and-white flickering occurs on the screen. In order to eliminate such an inconvenience in the present invention, the following countermeasures are taken. More specifically, computer 211, capable of key-inputting image retrieval data, is connected to image recording unit 212, as shown in FIG. 8. Recording unit 212 has a recording medium, such as a frame memory, and a recording/reproduction head so that it can record an image signal obtained from, e.g., an electronic endoscope and reproduce a recorded image.

Computer 211 can output a readout command signal and an image switching signal in response to key-in of the retrieval code. The image switching signal output terminal of computer 211 together with the image output terminal of image recording unit 212 is connected to synchronizing circuit 213. Synchronizing circuit 213 is provided to synchronize frames, and an output terminal thereof is connected to switching circuit 214 and sync signal generator 216. Switching circuit 214 has two switching terminals that are switched by a timing signal from synchronizing circuit 213. These switching terminals are respectively connected to image recording unit 212 and black frame signal generator 217. The common terminal of switching circuit 214 is connected to image monitor 215. Generator 217 is connected to the output terminal of sync signal generator 216 and outputs a black image signal in synchronism with a sync signal.

Figure 9:
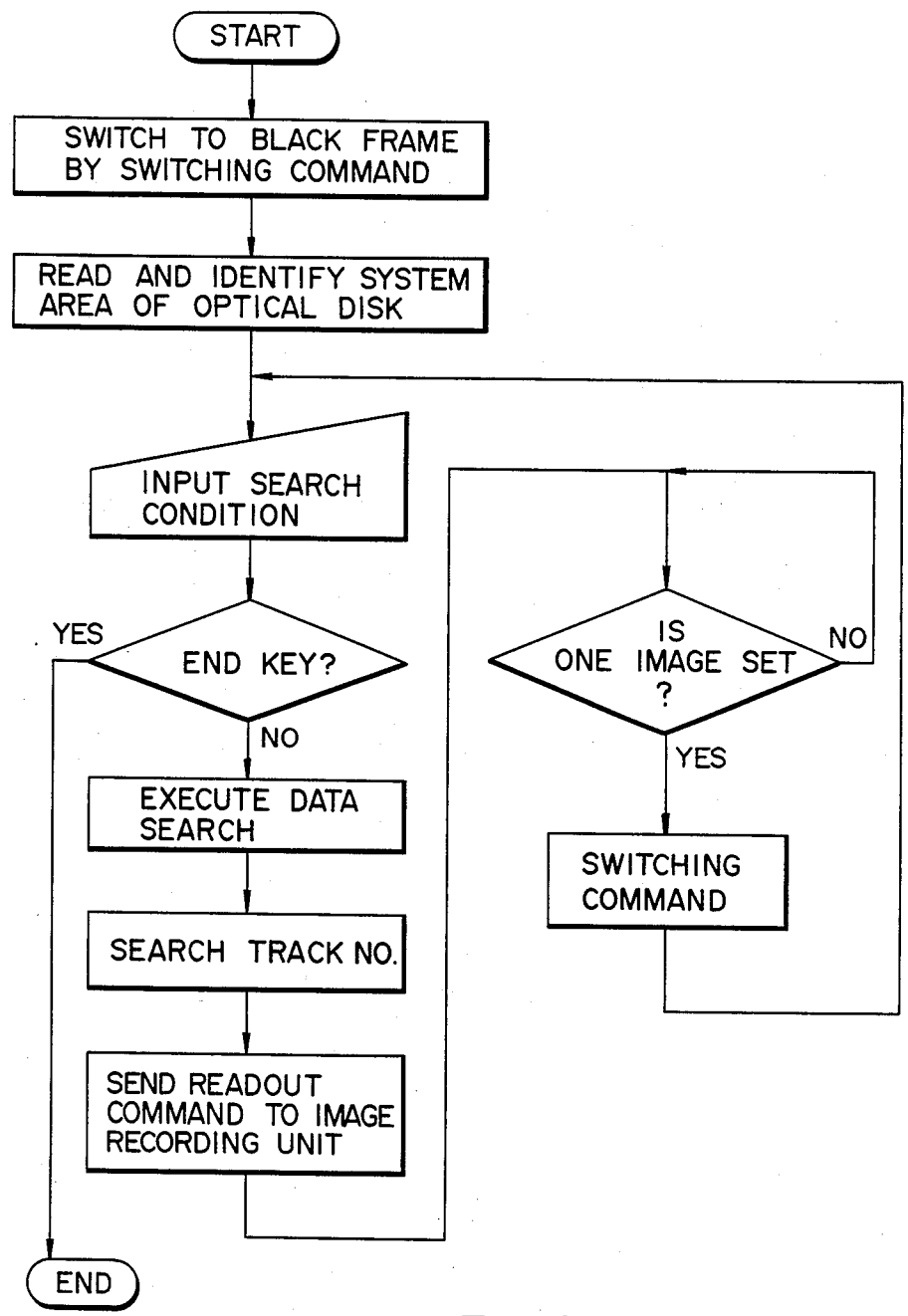
FIG. 9 is a flow chart for explaining the operation of the unit shown in FIG. 8.

The operation of the above imaging apparatus will be described with reference to the flow chart of FIG. 9. In response to a start command, i.e., operation of a reproduction execution key, computer 211 outputs an image switching command signal to synchronizing circuit 213. Synchronizing circuit 213 inputs a switching timing signal to switching circuit 214 in response to the switching command signal. In response to the timing signal, switching circuit 214 connects black frame signal generator 217 to monitor 215. In this case, sync signal generator 216 outputs a sync signal to generator 217 in response to an output signal from synchronizing circuit 213. Generator 217 outputs a black image signal synchronized with the sync signal. The black image signal is input to image monitor 215 through switching circuit 214 and displayed as a black image.

Only when a desired optical disk is searched for, computer 211 identifies the optical disks by the data (binary code data) read out from the system program areas (retrieval code tracks) of the optical disks. The system program area has a format as follows:

```
23986                              24000
     | 7 frames | 4 frames | 4 frames |
       Disk No.   Spare    Registration No.
```

Retrieval conditions, e.g., patient's number, patient's name, frame number, and so on are input with the keys of computer 211. Image recording unit 212 executes data retrieval by a retrieval code corresponding to the retrieval conditions. When a track number corresponding to an image to be read out is retrieved, computer 211 supplies a readout command signal to image recording unit 212. In response to the readout command signal, recording unit 212 reads out image data from a retrieved image recording track of the optical disk. When 1-frame image data is read, computer 211 outputs a switching command signal and switches the terminal of switching circuit 214 to the side of recording unit 212. Therefore, an image signal from recording unit 212 is input to image monitor 215, and an endoscopic image is displayed on monitor 215. In this case, in response to the switching command signal, sync signal generator 216 stops signal oscillation. As a result, black frame signal generator 217 stops generating a black frame signal.

When, e.g., another frame number is input as a retrieval condition, the operation similar to above is performed, and a new 1-frame image is displayed on monitor 215. When a retrieval condition is input and then an end key is depressed to cancel it, image retrieval and readout are completed.

When the monitor is switched to the black frame signal generator side at the time of start, i.e., at the start of image reproduction and a black image is displayed, since a non-required image is not displayed before retrieval, the user may not erroneously determine the image, and flickering caused by retrieval data does not occur on the screen.

In the above embodiment, a black image or a specific image, is displayed. The specific image can be a white image, a color bar chart, a gray scale, or the like. Also, a message, for example, "during retrieving" can be superimposed on the specific image. The image generator can be incorporated on a single circuit board as the switching circuit.

Since the image output means for outputting an image of a predetermined pattern is provided, in addition to the main image output unit, so that a predetermined pattern is displayed before retrieval of a desired image, an erroneous determination on the display image of the monitor screen and flickering of the screen can be avoided.

What is claimed is:

1. An endoscope video apparatus comprising:
   image signal output means, provided to an endoscope, for outputting an endoscopic image signal;
   video processing means for processing the image signal and outputting a video signal;
   video recording means for recording the video signal from said video processing means;
   input means for inputting retrieval data corresponding to the video signal recorded in said video recording means;
   informing means for informing the retrieval data to said video recording means;
   discriminating means for discriminating presence/absence of the retrieval data from said input means and outputting discrimination data; and
   means for outputting alarm data in response to the discrimination data representing absence of retrieval data from said discriminating means.

2. An apparatus according to claim 1, wherein said informing means includes communication means for transmitting the retrieval data from said input means to said video recording means.

3. An apparatus according to claim 1, wherein said video processing means includes character output means for outputting character data, said video recording means for recording the video signal, and means for combining the character data with the video signal and outputting an obtained composite image signal.

4. An apparatus according to claim 3, wherein said character data output means has a memory for storing retrieval data input from said input means and readout means for reading out the retrieval data from said memory.

5. An apparatus according to claim 1, wherein said discriminating means includes means for recording the retrieval data input by said input means, and means for identifying the retrieval data in said recording means and outputting to said video recording means an image-recording enable signal together with the retrieval data through said informing means.

6. An apparatus according to claim 5, wherein said alarm data output means comprises a sound producing member for producing an alarm in response to the discrimination data representing the absence of retrieval data.

7. An apparatus according to claim 1, wherein said video recording means has a recording means for recording a video signal, detecting means for detecting a number of recordable frames, comparing means for comparing the number of frames detected by said detecting means with a predetermined number of frames, and means for inhibiting video recording by said video recording means in response to resultant data supplied from said comparing means and representing that the number of recordable frames is not more than the predetermined number.

8. An apparatus according to claim 7, wherein said inhibiting means has means for displaying a message representing inhibition of video recording.

9. An apparatus according to claim 1, further comprising means for outputting a specific image signal different from the endoscopic image signal, and wherein said video processing means has means for performing selective switching between the endoscopic image signal and the specific image signal and outputting a selected signal to said display means.

10. An apparatus according to claim 9, wherein said switching means is means for guiding the specific image signal corresponding to a specific image to said display means in response to start of readout of the video signal from said video recording means.

11. An apparatus according to claim 9, wherein said specific image output means is means for outputting an image signal representing a black image.

12. An apparatus according to claim 9, wherein said specific image output means is means for outputting an image signal representing a white image.

13. An apparatus according to claim 9, wherein said specific image output means is means for outputting an image signal representing a color bar chart.

14. An apparatus according to claim 9, wherein said specific image output means is means for outputting an image signal representing a gray scale chart.

15. An apparatus according to claim 9, further comprising means for synchronizing said specific image output means with said endoscopic image output means, and wherein said switching means is means operative in synchronism with a sync signal of an image signal supplied from said endoscopic image output means.

16. An apparatus according to claim 9, wherein said specific image output means and said switching means are formed on a single circuit board.

17. An apparatus according to claim 9, wherein said means for outputting a specific image signal includes means for producing a signal representing a message superimposed on the specific image.

* * * * *